(12) United States Patent
Greene et al.

(10) Patent No.: US 11,426,256 B2
(45) Date of Patent: Aug. 30, 2022

(54) IMPLANTABLE MARKERS, AND SYSTEMS AND METHODS FOR USING THEM

(71) Applicant: CIANNA MEDICAL, INC., Aliso Viejo, CA (US)

(72) Inventors: John E. Greene, Valley Center, CA (US); Nikolai Rulkov, San Diego, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 648 days.

(21) Appl. No.: 15/446,944

(22) Filed: Mar. 1, 2017

(65) Prior Publication Data
US 2017/0252124 A1    Sep. 7, 2017

Related U.S. Application Data

(60) Provisional application No. 62/303,312, filed on Mar. 3, 2016.

(51) Int. Cl.
*A61B 90/00* (2016.01)
*A61B 17/00* (2006.01)
(Continued)

(52) U.S. Cl.
CPC .............. *A61B 90/39* (2016.02); *A61B 90/06* (2016.02); *A61B 90/08* (2016.02);
(Continued)

(58) Field of Classification Search
CPC ............ A61B 5/6861; A61B 2090/397; A61B 2034/2051; A61B 2090/306;
(Continued)

(56) References Cited

U.S. PATENT DOCUMENTS 5,190,059 A * 3/1993 Fabian .................. A61B 90/39
                                                              606/1
5,361,070 A    11/1994 McEwan
(Continued)

FOREIGN PATENT DOCUMENTS

EP        1374793 A1    2/2004
EP        1510183 A1    3/2005
(Continued)

OTHER PUBLICATIONS

Ahmadian et al., Miniature Transmitter for Implantable Micro Systems, Sep. 2003, Proceedings of the 25th Annual International Conference of the IEEE EMBS (Year: 2003).*
(Continued)

*Primary Examiner* — Amelie R Davis
*Assistant Examiner* — Helene Bor
(74) *Attorney, Agent, or Firm* — Dorsey & Whitney LLP (57) ABSTRACT

Markers, probes, and related systems and methods are provided for localizing locations within a patient's body, e.g., a lesion within a breast. The marker includes an energy converter e.g., one or more photodiodes, for transforming light energy striking the marker into electrical energy, a storage device coupled to the energy converter for storing the electrical energy, a threshold element that closes a switch when the electrical energy reaches a predetermined threshold to discharge the electrical energy and cause the antenna to transmit a radio frequency (RF) signal. The system includes a probe that transmits light into the patient's body and a processor that correlate the frequency of the RF signals to a distance from the probe to the marker.

19 Claims, 3 Drawing Sheets

(51) Int. Cl.
*A61B 34/20* (2016.01)
*A61B 90/30* (2016.01)

(52) U.S. Cl.
CPC .............. *A61B 2017/00115* (2013.01); *A61B 2017/00199* (2013.01); *A61B 2017/00411* (2013.01); *A61B 2034/2051* (2016.02); *A61B 2090/061* (2016.02); *A61B 2090/0807* (2016.02); *A61B 2090/306* (2016.02); *A61B 2090/3908* (2016.02); *A61B 2090/3925* (2016.02); *A61B 2090/3945* (2016.02); *A61B 2090/3966* (2016.02); *A61B 2090/3975* (2016.02); *A61B 2090/3987* (2016.02)

(58) Field of Classification Search
CPC .... A61B 2090/3908; A61B 2090/3925; A61B 2090/3945; A61B 2090/3975; A61B 2090/3987; A61B 2090/3991; A61B 2017/00115; A61B 2017/00199; A61B 2017/00411; A61B 5/064; A61B 5/4312; A61B 5/6847; A61B 90/06; A61B 90/08; A61B 90/98
See application file for complete search history.

(56) References Cited

U.S. PATENT DOCUMENTS

| | | | |
|---|---|---|---|
| 5,573,012 A | 11/1996 | McEwan | |
| 5,764,162 A | 6/1998 | Ehrlich | |
| 5,766,208 A | 6/1998 | McEwan | |
| 5,853,366 A | 12/1998 | Dowlatshahi | |
| 5,879,357 A | 3/1999 | Heaton et al. | |
| 6,144,300 A | 11/2000 | Dames | |
| 6,226,548 B1 | 5/2001 | Foley | |
| 6,233,479 B1 | 5/2001 | Haddad et al. | |
| 6,363,940 B1 | 4/2002 | Krag | |
| 6,492,933 B1 | 12/2002 | McEwan | |
| 6,496,717 B2 | 12/2002 | Cox et al. | |
| 6,575,991 B1 | 6/2003 | Chesbrough et al. | |
| 6,725,083 B1 | 4/2004 | Burbank et al. | |
| 6,898,464 B2* | 5/2005 | Edell ................ | A61B 5/0017 128/903 |
| 6,914,552 B1 | 7/2005 | McEwan | |
| 7,174,201 B2 | 2/2007 | Govari et al. | |
| 7,569,065 B2 | 8/2009 | Chesbrough et al. | |
| 8,052,708 B2 | 11/2011 | Chesbrough et al. | |
| 9,713,437 B2 | 7/2017 | Fullerton | |
| 9,987,097 B2* | 6/2018 | van der Weide ...... | A61B 90/98 |
| 2002/0077553 A1* | 6/2002 | Govari ................. | A61B 5/0031 600/486 |
| 2003/0004411 A1 | 1/2003 | Govari et al. | |
| 2003/0018246 A1 | 1/2003 | Govari et al. | |
| 2003/0088186 A1 | 5/2003 | Doody | |
| 2003/0192557 A1 | 10/2003 | Krag et al. | |
| 2004/0054385 A1 | 3/2004 | Lesho | |
| 2005/0036945 A1 | 2/2005 | Thomas et al. | |
| 2005/0059884 A1 | 3/2005 | Krag | |
| 2005/0096589 A1 | 5/2005 | Shachar | |
| 2006/0025795 A1 | 2/2006 | Chesbrough et al. | |
| 2006/0258933 A1 | 11/2006 | Ellis et al. | |
| 2007/0038014 A1 | 2/2007 | Cox et al. | |
| 2007/0093726 A1 | 4/2007 | Leopold et al. | |
| 2007/0100666 A1 | 5/2007 | Stivoric | |
| 2007/0135711 A1 | 6/2007 | Chernomorsky | |
| 2007/0195929 A1 | 8/2007 | Ruchala | |
| 2007/0243225 A1 | 10/2007 | McKay | |
| 2008/0027313 A1 | 1/2008 | Shachar | |
| 2008/0071169 A1 | 3/2008 | Craddock et al. | |
| 2008/0086046 A1* | 4/2008 | Petcavich ................ | A61B 5/06 600/373 |
| 2008/0200802 A1 | 8/2008 | Bhavaraju et al. | |
| 2008/0269601 A1 | 10/2008 | Schwamb | |
| 2008/0281190 A1 | 11/2008 | Petcavich et al. | |
| 2009/0015832 A1 | 1/2009 | Popovic et al. | |
| 2009/0157068 A1 | 6/2009 | Kallel et al. | |
| 2009/0216115 A1 | 8/2009 | Seilar | |
| 2009/0248014 A1 | 10/2009 | Shachar et al. | |
| 2009/0281422 A1 | 11/2009 | Salama et al. | |
| 2009/0299174 A1 | 12/2009 | Wright et al. | |
| 2010/0004523 A1 | 1/2010 | August et al. | |
| 2010/0118779 A1 | 5/2010 | Umesh et al. | |
| 2010/0234792 A1 | 9/2010 | Dacey | |
| 2010/0275934 A1* | 11/2010 | Keren .................. | G01D 5/2066 324/228 |
| 2011/0166442 A1* | 7/2011 | Sarvazyan ............. | A61B 34/20 600/424 |
| 2011/0313288 A1 | 12/2011 | Chi Sing | |
| 2014/0309522 A1* | 10/2014 | Fullerton ............... | A61B 5/064 600/424 |
| 2015/0349150 A1* | 12/2015 | Carey ............... | H01L 27/14629 257/432 |
| 2016/0294056 A1* | 10/2016 | Manteghi ................. | H04B 1/04 |
| 2017/0007352 A1* | 1/2017 | King ..................... | A61B 90/90 |
| 2020/0390364 A1 | 12/2020 | Greene et al. | |

FOREIGN PATENT DOCUMENTS

| | | |
|---|---|---|
| WO | 200134049 | 5/2001 |
| WO | 0239918 A1 | 5/2002 |
| WO | 2004032779 A1 | 4/2004 |
| WO | 2007087447 A2 | 8/2007 |
| WO | 2007117478 A2 | 10/2007 |
| WO | 2014149183 | 9/2014 |
| WO | 2017151808 | 9/2017 |
| WO | 2018222777 | 12/2018 |

OTHER PUBLICATIONS http://www.theradarreflectorsite.org/WebManuscript, Chapter 6: Passive Radar Reflector Elements, 18 pages (pp. 64-81).
Hughes, Jenevieve H. et al., A Multi-site Vlidation Trial of Radioactive Seed Localization as an Alternative to Wire Localization, The Breast Journal, vol. 14 No. 2, 2008 Blackwell Publishing, Inc., 5 pages.
Nilavalan, R. et al., Wideband Microstrip Patch Antenna Desiign for Breast Cancer Tumour Detection, IEEE Xplore/IEEE.org, Apr. 30, 2007, Institution of Engineering and Technology, 1 page.
Stephan, Pam, Wire Localization Procedure—Breast Biopsy or Lumpectomy, About.com/Breast Cancer, Sep. 3, 2008, American Cancer Society/Ohio State Medical Center, 2 pages.
Azevedo, Stephen & Thomas E. McEwan, Micropower Impulse Radar, Science & Technology Review, Jan./Feb. 1996, 7 pages.
Huger, Ingrid, et al., ultraMEDIS—Ultra-Wideband Sensing in Medicine, INTECH, 2013, 66 pages.
Yun, Xing, et al., Broadband Cross-Polarized Bowtie Antenna . . . , Dept. of Electrical and Computer Engineering, University of Calgary, Calgary, Alberta, CA, 2003 IEEE, pp. 1091-1094, 4 pages.
Shannon, C.J., et al., Dialectric-Filled Slotline Bowtie Antenna for Breast Cancer Detection, Electronics Letters, Mar. 31, 2005, vol. 41, No. 7, 2 pages.
Hagness, Susan C., et al., Three-Dimensional FDTD Analysis of a Pulsed Microwave Confocal System for Breast Dancer Detection, IEEE Transactions on Antennas and Propagation, vol. 47, No. 5, May 1999, 9 pages.
Krishnan, Sivanand, et al., UWB-IR Active Reflector for High Precision Ranging and Positioning Applications, Institute of Infocomm Research, A*Star Singapore, 2010 IEEE, pp. 14-18, 5 pages.
European Patent Office, Forms PCT/ISA/220, /210, & /237, International Search Report and Written Opinion foi Corresponding International Application No. PCT/US2017/020260, Applicant: Cianna Medical, Inc., dated May 11, 2017, 17 pages.
International Search Report and Written Opinion dated Sep. 20, 2018 for PCT/US2018/035219.
Office Action dated Nov. 27, 2019 for U.S. Appl. No. 15/993,559.
Notice of Allowance dated Apr. 8, 2020 for U.S. Appl. No. 15/993,559.
Office Action dated Feb. 14, 2022 for U.S. Appl. No. 16/881,893.

* cited by examiner

IMPLANTABLE MARKERS, AND SYSTEMS AND METHODS FOR USING THEM

RELATED APPLICATION DATA

The present application claims benefit of provisional application Ser. No. 62/303,312, filed Mar. 3, 2016, the entire disclosure of which is expressly incorporated by reference herein.

FIELD OF THE INVENTION

The present invention relates to implantable markers or tags, and to systems and methods for localizing such markers within a patient's body, e.g., during surgical procedures or other procedures, such as during lumpectomy procedures.

BACKGROUND

Before a biopsy or surgical procedure to remove a lesion within a breast, e.g., during a lumpectomy procedure, the location of the lesion must be identified. For example, mammography or ultrasound imaging may be used to identify and/or confirm the location of the lesion before the procedure. The resulting images may be used by a surgeon during the procedure to identify the location of the lesion and guide the surgeon, e.g., during dissection to access and/or remove the lesion. However, such images are generally two dimensional and therefore provide only limited guidance for localization of the lesion since the breast and any lesion to be removed are three-dimensional structures. Further, such images may provide only limited guidance in determining a proper margin around the lesion, i.e., defining a desired specimen volume to be removed.

To facilitate localization, immediately before a procedure, a wire may be inserted into the breast, e.g., via a needle, such that a tip of the wire is positioned at the location of the lesion. Once the wire is positioned, it may be secured in place, e.g., using a bandage or tape applied to the patient's skin where the wire emerges from the breast. With the wire placed and secured in position, the patient may proceed to surgery, e.g., to have a biopsy or lumpectomy performed.

One problem with using a wire for localization is that the wire may move between the time of placement and the surgical procedure. For example, if the wire is not secured sufficiently, the wire may move relative to the tract used to access the lesion and consequently the tip may misrepresent the location of the lesion. If this occurs, when the location is accessed and tissue removed, the lesion may not be fully removed and/or healthy tissue may be unnecessarily removed. In addition, during the procedure, the surgeon may merely estimate the location of the wire tip and lesion, e.g., based on mammograms or other images obtained during wire placement, and may proceed with dissection without any further guidance. Again, since such images are two dimensional, they may provide limited guidance to localize the lesion being treated or removed.

Alternatively, it has been suggested to place a radioactive seed to provide localization during a procedure. For example, a needle may be introduced through a breast into a lesion, and then a seed may be deployed from the needle. The needle may be withdrawn, and the position of the seed may be confirmed using mammography. During a subsequent surgical procedure, a hand-held gamma probe may be placed over the breast to identify a location overlying the seed. An incision may be made and the probe may be used to guide excision of the seed and lesion.

Accordingly, apparatus and methods for localization of lesions or other tissue structures in advance of and/or during surgical, diagnostic, or other medical procedures would be useful.

SUMMARY

The present invention is directed to implantable markers and tags, and to systems and methods for localizing such markers within a patient's body, e.g., during surgical procedures or other procedures, such as during lumpectomy procedures.

In accordance with one embodiment, a marker is provided sized for introduction into a target tissue region within a patient's body that includes an energy converter for transforming light energy striking the marker into electrical energy; a switch; an antenna coupled to the switch; and a storage circuit coupled to the energy converter for storing electrical energy generated by the energy converter until a predetermined threshold is achieved, the storage circuit coupled to the switch for closing the switch when the predetermined threshold is achieved to deliver electrical energy to the antenna, whereupon the antenna transmits a radio frequency (RF) signal.

In accordance with another embodiment, a marker is provided sized for introduction into a target tissue region within a patient's body that includes one or more photosensitive diodes to convert light received from a light source outside a patient's body into electrical energy; an antenna; and a circuit comprising a capacitor coupled to the one or more photosensitive diodes for storing the electrical energy, a threshold element coupled to the capacitor and a switch, the threshold element configured to close the switch when the electrical energy stored by the capacitor reaches a threshold voltage to deliver electrical energy to the antenna, whereupon the antenna transmits a radio frequency (RF) pulse.

In accordance with still another embodiment, a system is provided for localizing a marker within a body that includes a marker sized for introduction into a target tissue region within a patient's body comprising an energy converter for transforming light energy striking the marker into electrical energy, a switch, an antenna coupled to the switch, and a storage circuit coupled to the energy converter for storing electrical energy generated by the energy converter until a predetermined threshold is achieved, the storage circuit coupled to the switch for closing the switch when the predetermined threshold is achieved to deliver electrical energy to the antenna, whereupon the antenna transmits a radio frequency (RF) signal; a probe comprising a light source configured to transmit a transmit light into the patient's body towards the marker; a receive antenna configured to receive the RF signal transmitted by the marker; a processor coupled to the receive antenna for correlating a frequency of the RF signals from the marker to a distance from the probe to the target tissue region within which the marker is introduced; and an output device coupled to the processor for providing information related to the distance.

In accordance with yet another embodiment, a method is provided for localization of a target tissue region within a patient's body that includes implanting a marker within a patient's body, the marker comprising an energy converter, an antenna, and a circuit coupled to the energy converter and the antenna; placing a probe adjacent the patient's body oriented towards the marker; activating the probe to deliver light energy into the patient's body such that the energy converter transforms the light energy into electrical energy that is periodically delivered to the RF antenna via the circuit such that the RF antenna transmits RF pulses; and correlating a frequency of the RF pulses to a distance from the probe to the marker.

Other aspects and features of the present invention will become apparent from consideration of the following description taken in conjunction with the accompanying drawings.

BRIEF DESCRIPTION OF THE DRAWINGS

These and other features, aspects, and advantages of the present disclosure will become better understood with regard to the following description, appended claims, and accompanying drawings where:

DETAILED DESCRIPTION OF THE EXEMPLARY EMBODIMENTS

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Figure 1:
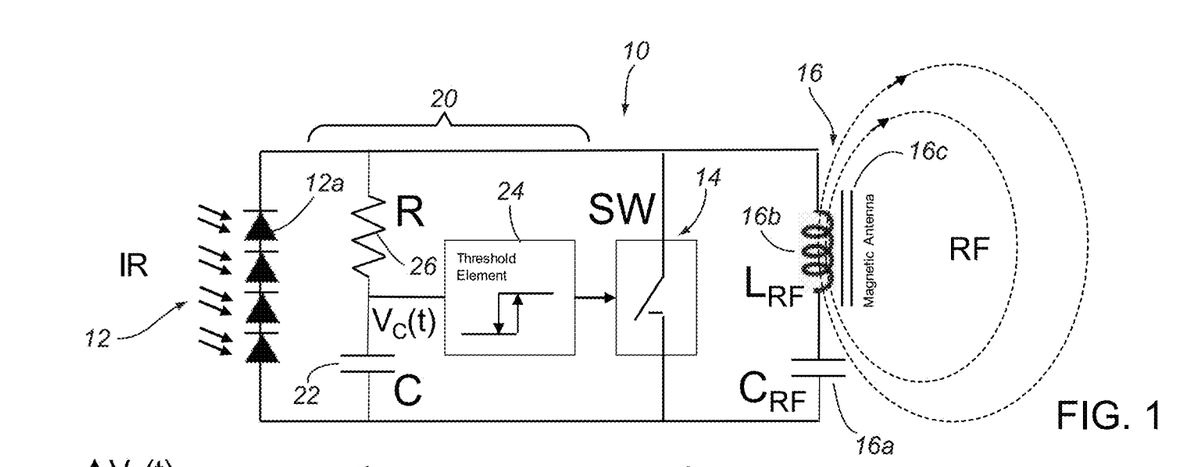
FIG. 1 is a schematic of an exemplary embodiment of a marker for implantation within a patient's body.
Figure 3A:
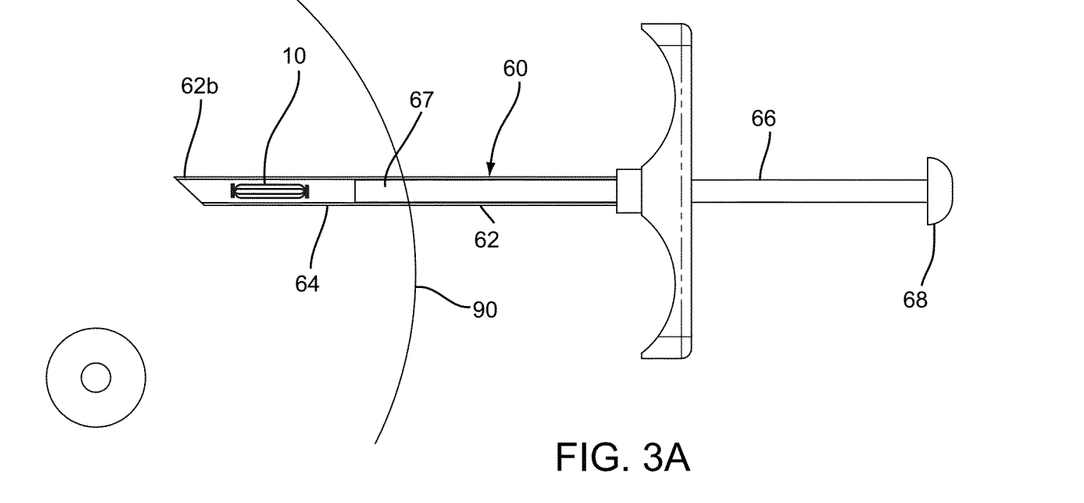
FIGS. 3A and 3B are side views of a breast, showing a delivery device being used to deliver a marker into tissue within the breast.
Figure 3B:
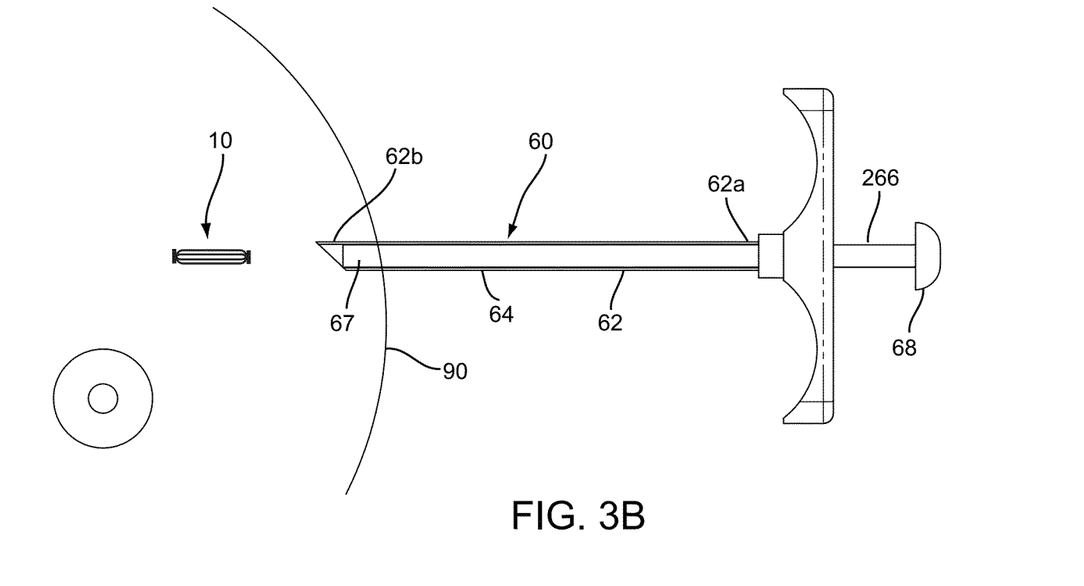
Figure 4:
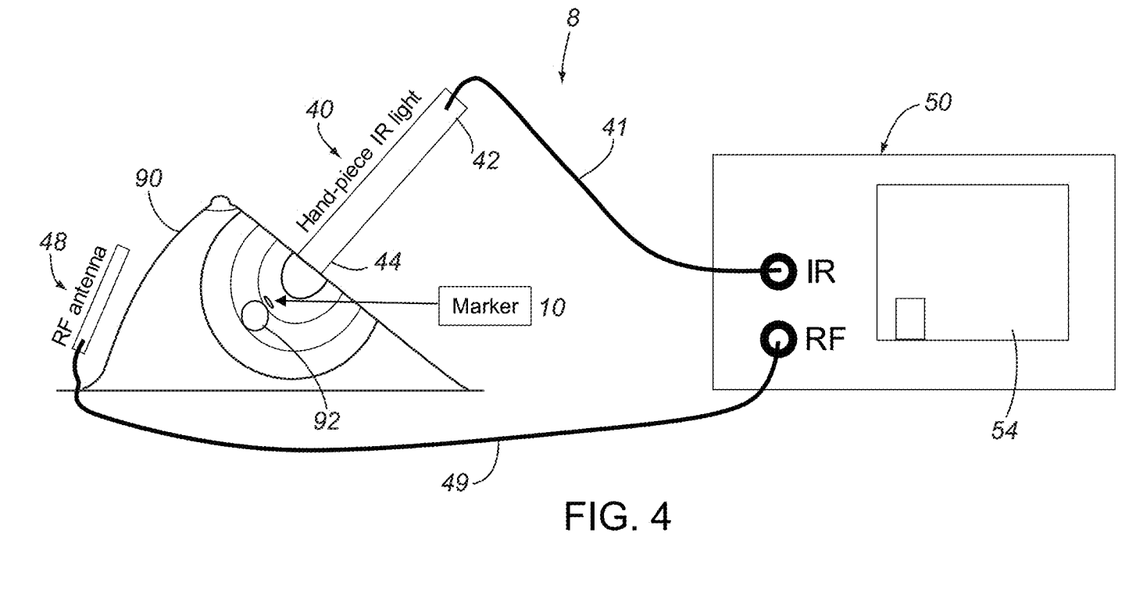
FIG. 4 is a side view of an exemplary embodiment of a system including a probe and display for identifying and/or locating a target implanted within a breast.

Turning to the drawings, FIG. 1 shows an exemplary embodiment of a marker or tag 10 that may be implanted within a patient's body, such as within a breast 90, e.g., as shown in FIG. 4. Generally, the marker 10 includes an energy converter 12, a switch 14, an antenna 16 coupled to the switch 14, and a storage circuit 20 coupled to the energy converter 12 for storing electrical energy generated by the energy converter 12 until a predetermined threshold is achieved, the storage circuit 20 coupled to the switch 14 for closing the switch 14 when the predetermined threshold is achieved to activate the antenna 16. The marker 10 may be included in a system 8 for performing a procedure, such as a lumpectomy procedure, e.g., including a delivery device 60 for delivering one or more of the markers into tissue, e.g., as shown in FIGS. 3A and 3B, a light transmitter or probe 40 for transmitting energy to the marker 10, a receive antenna 48 for detecting signals from the marker antenna 16, and a controller or processing unit 50, e.g., as shown in FIG. 4 and described further below.

The components of the marker 10 may be encased or embedded in an electronics package or housing (not shown) sized and configured for implantation within a patient's body. For example, a semiconductor chip, print circuit board (PCB), and/or other circuit may be carried in the package that includes the energy converter 12, the switch 14, and the storage circuit 20. The antenna 16 may be contained within the package or may be located at least partially outside the package.

Returning to FIG. 1, in an exemplary embodiment, the energy converter 12 includes a plurality of photosensitive diodes 12*a*, e.g., connected in series, capable of transforming incident light striking them into electrical energy. Optionally, the diodes 12*a* may be provided in multiple pairs of diodes connected in series, which may be arranged orthogonally to one another spatially within the package (not shown). For example, given that photosensitive diodes are directional, at least two pairs of diodes may be mounted within the package offset one hundred eighty degrees (180°) or otherwise relative to one another such that at least one pair of diodes 12*a* may receive light from the probe 40 regardless of the orientation of the marker 10 relative to the probe 40 after implantation. The package may be at least partially transparent or the diodes 12*a* may be exposed from the package such that light directed towards the package may be received by the diodes 12*a*.

In an exemplary embodiment, the diodes 12*a* may be configured to convert infrared light to electrical energy. One advantage of infrared energy is that it may pass sufficiently through tissue such that the probe 40, when placed against a patient's skin, may deliver sufficient energy to activate a relatively small marker 10, e.g., when implanted several inches away within the patient's body, e.g., breast 90, as shown in FIG. 6. Further, because the infrared light is partially absorbed by tissue, the intensity of the light decreases the further the light passes into tissue. This principle may be used to correlate the distance to the marker from the probe 40, as described elsewhere herein.

Optionally, the diodes 12*a* (and/or a transparent surface of the package overlying the diodes 12*a*) may include one or more coatings and/or filters. For example, a coating may be applied that modifies the absorption rate of the diodes 12*a*, e.g., to provide predetermined charging rates for the storage circuit 20 and/or activation intervals of the antenna 16, e.g., based on desired distances between the probe 40 and the marker 10. In an exemplary embodiment, if desired, a coating may be provided on the diodes 12*a* to slow the charging rate and consequently the time interval of the signals transmitted by the antenna 16 for a given intensity of light striking the diodes 12*a*.

In addition or alternatively, in some applications, multiple markers may be provided having different filters on the diodes 12*a*, e.g., to facilitate distinguishing the markers from one another. For example, each marker may include a filter that passes only a segment of the infrared wavelengths of light such that each marker only absorbs a unique segment of infrared light striking the diodes 12*a*. Thus, if a probe is provided that selectively delivers different segments of infrared light, the probe may be operated to transmit a segment of infrared light that activates a target marker that includes a filter passing that segment. The probe may sequentially or otherwise intermittently transmit each desired segment of infrared light to activate and identify each marker of a set of markers implanted within the patient's body.

Returning to FIG. 1, the storage circuit 20 generally includes a storage capacitor or other storage device 22 and a threshold element 24 coupled to the capacitor 22 and the switch 14. For example, as shown, the storage capacitor 22 and a resistor 26 may be coupled to the opposite ends of the energy converter 12 to provide a charging circuit such that electrical energy generated by the diodes 12*a* charges the storage capacitor 22. The threshold element 24 is configured such that, when the storage capacitor 22 reaches a predetermined threshold, e.g., maximum voltage, the threshold element 24 causes the switch 14 to close.

The switch 14 and antenna 16 are connected in parallel with the storage capacitor 22 such that, with the switch 14 open, the antenna 16 remains dormant. However, when the switch 14 is closed, the electrical energy stored by the storage capacitor 22 is discharged causing the antenna 16 to transmit a signal. For example, as shown, the antenna 16 includes an LC circuit including an antenna capacitor 16a and an antenna inductor 16b coupled to a magnetic antenna 16c. Thus, when the switch 14 is closed, the energy discharged from the storage capacitor 22 causes the antenna 16 to transmit a radio frequency (RF) pulse or burst.

Figure 2:
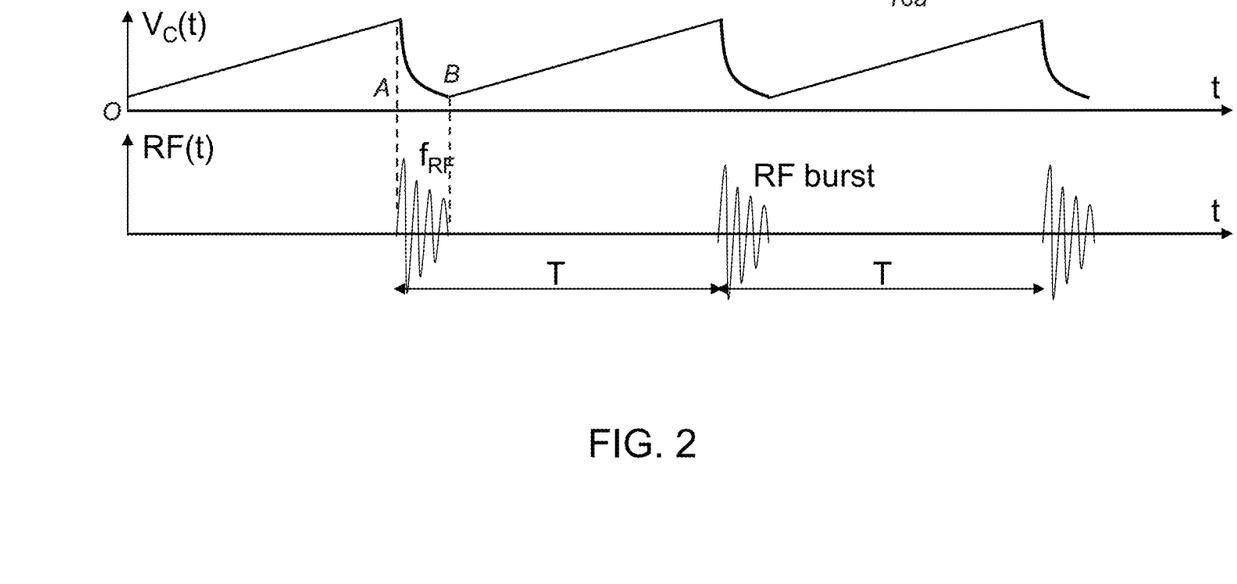
FIG. 2 is a graph showing operation of the marker of FIG. 1 in response to external stimulation.

FIG. 2 shows a representation of the operation of the marker 10 when exposed to light, e.g., infrared light, that is absorbed by the diodes 12a. Initially, at time 0 (upon initial exposure to light), the diodes 12a convert the absorbed light to electrical energy that charges the storage capacitor 22, e.g., causing an increase in voltage as shown by the Vc(t) portion of the graph. At time A, the voltage of the storage capacitor 22 reaches the predetermined threshold of the threshold element 24, whereupon the threshold element 24 closes the switch 14. This causes the storage capacitor 22 to discharge, reducing the voltage until time B. The resulting discharge causes the antenna 16 to transmit a RF pulse, as shown by the RF(t) portion of the graph.

Once the storage capacitor 22 is discharged, the threshold element 24 opens the switch 14 again, whereupon the storage capacitor 22 begins to charge again, as shown in the Vc(t) portion of the graph after B. This cycle may repeat as long as the energy converter 12 continues to be exposed to and absorbs light. As shown in the RF(t) portion of the graph, a time interval or frequency T of the RF pulses may be determined, which may be correlated to the distance from the light source to the marker 10, as described further below.

Turning to FIGS. 3A and 3B, a needle or delivery device 60 may be provided for introducing one or more markers 10 (one marker shown) into a patient's body, e.g., into a breast 90 adjacent a lesion 92. For example, the delivery device 60 may include a shaft 62 including a proximal end 62a and a distal end 62b sized for introduction through tissue into a target tissue region (not shown) and carrying the marker(s) 10. The delivery device 60 may include a lumen 64 extending at least partially between the proximal and distal ends 62a, 62b of the shaft 62, and a pusher member 66 slidable within the shaft 62 for selectively delivering one or more markers 10 successively or otherwise independently from the lumen 64.

As shown, the distal end 62b of the shaft 62 may be beveled, pointed, and/or otherwise sharpened such that the shaft 62 may be introduced directly through tissue. Alternatively, the delivery device 60 may be introduced through a cannula, sheath, or other tubular member (not shown) previously placed through tissue. Optionally, the distal end 62b may include a band or other feature, e.g., formed from radiopaque, echogenic, or other material, which may facilitate monitoring the distal end 62b during introduction, e.g., using fluoroscopy, ultrasound, electromagnetic signals, and the like.

As shown, the pusher member 66 includes a piston or other element 67 disposed within the lumen 64 adjacent the marker(s) 10 and a plunger or other actuator 68 coupled to the piston to push the marker(s) 10 from the lumen 64. For example, as shown in FIG. 3A, the distal end 62a of the shaft 62 (carrying the marker 10 therein) may be inserted into a breast 90 (or other tissue) and advanced or otherwise positioned to place the marker 10 at a target location, e.g., within or otherwise adjacent a cancerous lesion 92. Optionally, external imaging may be used to confirm the location of the marker 10 relative to the lesion 92. Once at the target location, the shaft 62 may be withdrawn relative to the pusher member 66, thereby deploying the marker 10, as shown in FIG. 3B. Optionally, the delivery device 60 may carry multiple markers (not shown), and the shaft 62 may be repositioned one or more times to deploy additional markers.

Alternatively, if desired, the pusher member 66 may be advanced to deploy the marker(s) 10 successively from the lumen 64, rather than retracting the shaft 62. In another alternative, a trigger device or other automated actuator (not shown) may be provided on the proximal end 62a of the shaft 62, which may retract the shaft 62 sufficiently with each activation, e.g., to delivery an individual marker 10 from the distal end 62b. Exemplary embodiments of delivery devices that may be used are described in U.S. Publication No. 2011/0021888, the entire disclosure of which is expressly incorporated by reference herein.

Turning to FIG. 4, an exemplary embodiment of a system 8 is shown for localization of a target tissue region within a patient's body, such as a tumor, lesion, or other tissue structure 92 within a breast 90 or other location within a body. As shown in FIG. 8, the system generally includes a probe 40 for transmitting light into the patient's body, a receive antenna 48, and a controller 50 and/or display unit 54 coupled to the probe 40, e.g., using one or more cables 41, 49.

As shown, the probe 40 may be a handheld device including a first or proximal end 42 configured to be held by a user, and a second or distal end 44 intended to be placed against or adjacent tissue, e.g., including a substantially flat or other contact surface. In addition, the probe 40 includes a light transmitter, e.g., a plurality of light fibers (not shown), configured to transmit light, e.g., infrared light into tissue contacted by the distal end 44, e.g., into breast tissue 90, as shown in FIG. 4. The light fibers may be coupled to a light source (not shown) within the controller 50, e.g., with the light fibers passing through the cable 41, or within the probe 40 itself, such that light from the light source passes through the light fibers distally from the distal end 44 of the probe 40. Alternatively, the light source may be located within the probe 40, e.g., adjacent the distal end 44 and one or more lenses, filters, or other components may be coupled to the light source to direct light from the distal end 44.

In an exemplary embodiment, the light source is an infrared light source, e.g., capable of delivering near infrared light between, for example, eight hundred and nine hundred fifty nanometers (800-950 nm) wavelength. Optionally, the light fibers may include one or more lenses, filters, and the like (not shown), if desired, for example, to focus the light transmitted by the probe 40 in a desired manner, e.g., in a relatively narrow beam extending substantially parallel to a central axis of the probe 40, in a wider beam, and the like.

In an alternative embodiment, the probe 40 may be configured to deliver different segments of wavelengths, e.g., within the infrared light range to selectively activate individual markers, as described elsewhere herein. For example, the probe 40 may transmit a first segment for a first period sufficient to activate and detect a first marker, then transmit a second segment for a second period sufficient to activate and detect a second marker, and the like.

The receive antenna 48 may be separate from the probe 40 such that the receive antenna 48 may be fixed and/or otherwise placed at a desired location sufficiently close to detect signals transmitted by the marker 10, e.g., on the patient's breast 90. For example, the receive antenna 48 may be a patch that may be adhered or otherwise secured to the patient's skin in a region near the breast 90, e.g., at a location away from the intended dissection path to the lesion 92. Thus, in this manner, the receive antenna 48 may remain substantially stationary and detect the RF pulses transmitted by the marker 10 and relay them to the controller 50 via the cable 49 for processing. Alternatively, a receive antenna may be provided within the probe 40 (not shown, which may detect and relay the signals to the controller 50 using the cable 41 (or a separate cable).

The controller 50 generally includes the light source to generate the light transmitted by the probe 40 (unless the light source is located within the probe 40) and one or more controllers, circuits, and the like to process signals received from the receive antenna 48. The components of the controller 50 may include discrete components, solid state devices, programmable devices, software components, and the like, as desired.

The controller 50 may also include one or more output devices, such as a display 54 for displaying information to a user of the probe 40, e.g., spatial or image data relating to the distance from the distal end 44 of the probe 40 to the marker 10. In addition, the controller 50 may include one or more speakers to provide audible information, e.g., pulses or frequencies related to the distance and/or other outputs, as desired. Optionally, the controller 50 may include other features or components, such as one or more user interfaces, memory, transmitters, receivers, connectors, cables, power sources, and the like (not shown). For example, the controller 40 may include one or more batteries or other internal power sources for operating the light source (if provided within the probe 40). Alternatively, the probe 40 may include a cable that may be coupled to an external power source, e.g., standard AC power, for operating the components of the probe 40.

Optionally, a portion of the probe 40 may be disposable, e.g., a portion adjacent the distal end 44, or a disposable cover, sleeve, and the like (not shown) may be provided if desired, such that at least a proximal portion of the probe 40 may be reusable. Alternatively, the entire probe 40 may be a disposable, single-use device while the controller 50 may be used during multiple procedures by connecting a new probe 40 and receive antenna 48 to the controller 50, which may remain out of the surgical field yet remain accessible and/or visible, as desired.

The system 8 may be used during a medical procedure, for example, in a breast biopsy or lumpectomy procedure, e.g., to facilitate localization of a lesion or other target tissue region and/or to facilitate dissection and/or removal of a specimen from a breast 90 or other body structure. It should be noted that, although the marker 10 and system 8 is described as being particularly useful in localization of breast lesions, they may also be used in localization of other objects in other areas of the body.

Before the procedure, a target tissue region, e.g., a tumor or other lesion, may be identified using conventional methods. For example, a lesion 92 within a breast 90 may be identified, e.g., using mammography and/or other imaging, and a decision may be made to remove the lesion. The marker 10 may be implanted within the breast 90 within or adjacent the target lesion 92, e.g., using a needle or other delivery device, such as the delivery device 60 shown in FIGS. 3A and 3B. Optionally, multiple markers (not shown) may be implanted, if desired, e.g., around the lesion 92.

Once the marker(s) 10 is implanted, as shown in FIG. 4, the distal end 44 of the probe 40 may be placed against the patient's skin, e.g., against the breast 90. Light from the probe 40 may be delivered into the breast 90 such that the light strikes the energy converter 12 of the marker 10. As explained above, this causes the storage circuit 20 to repeatedly charge and discharge, causing the antenna 16 to transmit RF pulses or bursts, which may be detected by the receive antenna 48.

The controller 50 may process the received signals and correlate them with the distance from the probe 40 to the marker 10. For example, as explained above, the time interval or frequency T of the RF pulses (shown in FIG. 2) may be proportional to the distance. In particular, as the distance from the probe 40 to the marker 10 increases, the intensity of light striking the diodes 12*a* is reduced, which results in less electrical energy being generated and the storage capacitor 22 charging more slowly. The controller 50 may include a digital processor that process the signals from the receive antenna 48 to provide an output of relative distance or actual distance, which may be presented on the display 54 and/or other output device. For example, the display 54 may simply be a readout providing distance and/or other data, e.g., based on the relative distance from the probe 40 to the marker 10. The distance information may be displayed as a numerical value representing the distance in units of length, such as in inches (in.) or centimeters (cm). In addition or alternatively, a speaker on the controller 50 may produce an audible indication of distance, e.g., spaced-pulses that increase in speed as the probe 40 is closer to the marker 10.

Based on the distance data acquired and presented, the user may select a path from the skin towards the lesion 92, and tissue may then be dissected, e.g., by creating an incision in the patient's skin and dissecting intervening tissue to a desired depth, e.g., corresponding to a target margin around the lesion is reached. A tissue specimen may be excised or otherwise removed using conventional lumpectomy procedures, e.g., with the marker 10 remaining within the removed specimen. At any time, the distal end 44 of the probe 40 may be placed against the patient's tissue to verify the distance and/or approach towards the lesion 92. Once the lesion 92 (and marker 10) are removed, the receive antenna 48 may be removed from the patient's body.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A marker sized for introduction into a target tissue region within a patient's body, comprising:
   one or more photosensitive diodes to convert light received from a light source outside a patient's body into electrical energy;
   an antenna; and
   a circuit comprising:
   a capacitor coupled to the one or more photosensitive diodes for storing the electrical energy,
   a threshold element coupled to the capacitor, and
   a switch, wherein the circuit threshold element is configured to close the switch when the electrical energy stored by the capacitor reaches a threshold voltage, wherein when the switch closes the capacitor discharges to deliver electrical energy from the capacitor to the antenna, whereupon the antenna transmits a radio frequency (RF) pulse using the electrical energy from the capacitor,
   wherein the circuit is configured such that, when the one or more photosensitive diodes are exposed to light, the capacitor repeatedly charges causing the switch to intermittently close and the antenna to transmit intermittent RF pulses, an interval between the RF pulses being proportional to a distance from the light source to the target tissue region within which the marker is introduced, wherein as the distance from the light source to the marker increases, an intensity of the light striking the photosensitive diodes is reduced which results in less electrical energy being generated and the capacitor charging more slowly causing the capacitor to take longer to reach the threshold voltage resulting in the interval between the RF pulses being extended.

2. The marker of claim 1, wherein the one or more photosensitive diodes comprise multiple diodes arranged orthogonally relative to one another.

3. The marker of claim 1, wherein the one or more photosensitive diodes comprise a coating thereon for modifying a light absorption rate of the one or more photosensitive diodes, the coating providing a predetermined charging rate for the capacitor.

4. The marker of claim 1, wherein the one or more photosensitive diodes comprise a filter thereon for limiting wavelengths of light from the light source that are received by the one or more photosensitive diodes, wherein the filter causes the photosensitive diodes to absorb a unique segment of light to distinguish the marker from other markers.

5. The marker of claim 1, wherein the antenna comprises an inductor coupled to a magnetic antenna that is activated when the switch closes to transmit the RF pulse.

6. A marker sized for introduction into a target tissue region within a patient's body, comprising:
- an energy converter for transforming light energy striking the marker into electrical energy;
- a switch;
- an antenna coupled to the switch; and
- a storage circuit coupled to the energy converter for storing electrical energy generated by the energy converter until a predetermined threshold is achieved, the storage circuit coupled to the switch for closing the switch when the predetermined threshold is achieved, wherein when the switch closes the storage circuit discharges to deliver electrical energy from the storage circuit to the antenna, whereupon the antenna transmits a radio frequency (RF) signal using the electrical energy from the storage circuit,
- wherein the storage circuit is configured such that, when the energy converter is exposed to light, the storage circuit repeatedly charges until the predetermined threshold is reached, causing the switch to intermittently close and the antenna to transmit intermittent RF signals, a time interval of the RF signals being proportional to a distance from a light source to the target tissue region within which the marker is introduced, wherein as the distance from the light source to the marker increases, an intensity of the light striking the energy converter is reduced which results in less electrical energy being generated and the storage circuit charging more slowly causing the storage circuit to take longer to reach the predetermined threshold resulting in the time interval of the intermittent RF signals being extended.

7. The marker of claim 6, wherein the energy converter comprises one or more photosensitive diodes configured to convert light received from a light source outside the patient's body to generate electrical energy.

8. The marker of claim 7, wherein the one or more photosensitive diodes comprise multiple diodes arranged orthogonally relative to one another.

9. The marker of claim 7, wherein the one or more photosensitive diodes comprise a coating thereon for modifying a light absorption rate of the one or more photosensitive diodes.

10. The marker of claim 7, wherein the one or more photosensitive diodes comprise a filter thereon for limiting wavelengths of light from the light source that are received by the one or more photosensitive diodes.

11. The marker of claim 6, wherein the antenna comprises an inductor coupled to a magnetic antenna that is activated when the switch closes to transmit the RF signal.

12. A system for localizing a marker within a patient's body, comprising:
- a marker sized for introduction into a target tissue region within a patient's body comprising an energy converter for transforming light energy striking the marker into electrical energy, a switch, an antenna coupled to the switch, and a storage circuit coupled to the energy converter for storing electrical energy generated by the energy converter until a predetermined threshold is achieved, the storage circuit coupled to the switch for closing the switch when the predetermined threshold is achieved, wherein when the switch closes the storage circuit discharges to deliver electrical energy from the storage circuit to the antenna, whereupon the antenna transmits a radio frequency (RF) signal using the electrical energy from the storage circuit, wherein the storage circuit is configured such that, when the energy converter is exposed to light, the storage circuit repeatedly charges until the predetermined threshold is reached, causing the switch to intermittently close and the antenna to transmit intermittent RF signals;
- a probe comprising a light source configured to transmit a transmit light into the patient's body towards the marker;
- a receive antenna configured to receive the intermittent RF signals transmitted by the marker;
- a processor coupled to the receive antenna for correlating a frequency of occurrence of the intermittent RF signals from the marker to a distance from the probe to the target tissue region within which the marker is introduced, wherein as the distance from the light source to the marker increases, an intensity of the transmit light striking the energy converter is reduced which results in less electrical energy being generated and the storage circuit charging more slowly causing the storage circuit to take longer to reach the threshold voltage resulting in the frequency of occurrence of the intermittent RF signals to be reduced; and
- an output device coupled to the processor for providing information related to the distance.

13. The system of claim 12, wherein the output device comprises a display to present visual information representing the distance from the probe to the marker.

14. The system of claim 12, wherein the output device comprises a speaker to present audio information representing the distance from the probe to the marker.

15. The system of claim 12, wherein the energy converter comprises one or more photosensitive diodes configured to convert light from the light source to generate electrical energy stored by the storage circuit.

16. The system of claim 12, wherein the probe comprises a contact surface for placement against the patient's body, the light source configured to transmit light from the contact surface into the patient's body.

17. A method for localization of a target tissue region within a patient's body, comprising:
   implanting a marker within a patient's body, the marker comprising an energy converter, an RF antenna, and a circuit coupled to the energy converter and the RF antenna;
   placing a probe adjacent the patient's body oriented towards the marker;
   activating a light source on the probe to deliver light energy into the patient's body such that the energy converter transforms the light energy into electrical energy that is periodically delivered to the RF antenna via the circuit such that the RF antenna transmits intermittent RF pulses using the electrical energy transformed from the light energy, wherein the electrical energy is delivered to the RF antenna after a threshold voltage of electrical energy is converted; and
   correlating intervals of the intermittent RF pulses to a distance from the probe to the marker, wherein as the distance from the light source to the marker increases, an intensity of the light striking the energy converter is reduced which results in less electrical energy being converted resulting in more time until the threshold voltage is reached and resulting in the intervals of the intermittent RF signals being extended.

18. The method of claim 17, wherein delivering light energy into the patient's body comprises delivering infrared light into the patient's body, and wherein the energy converter comprises one or more photosensitive diodes that transform the infrared light into electrical energy.

19. The method of claim 17, wherein the circuit comprises a storage circuit coupled to a switch, and wherein the storage circuit stores the electrical energy from the energy converter until a threshold voltage is achieved, whereupon the storage circuit activates the switch to deliver electrical energy to the RF antenna to cause the RF antenna to transmit a RF pulse.

* * * * *